United States Patent [19]
Eller et al.

[11] Patent Number: 5,393,522
[45] Date of Patent: Feb. 28, 1995

[54] COMPOSITIONS FOR THE CONTROL OF PEPPER WEEVILS

[75] Inventors: Fred J. Eller, Metamora; Robert J. Bartelt, East Peoria, both of Ill.

[73] Assignee: The United States of America as represented by the Secretary of Agriculture, Washington, D.C.

[21] Appl. No.: 12,826

[22] Filed: Feb. 3, 1993

[51] Int. Cl.⁶ ................ A01N 31/04; A01N 35/02; A01N 37/06; A01N 31/02
[52] U.S. Cl. .................... 424/84; 514/557; 514/558; 514/560; 514/703; 514/729; 514/739; 424/195.1
[58] Field of Search ............ 514/729, 703, 739, 557, 514/560, 558; 424/84, 195.1

[56] References Cited

U.S. PATENT DOCUMENTS

| | | | |
|---|---|---|---|
| 3,657,414 | 4/1972 | Hedin et al. | 424/84 |
| 3,852,321 | 12/1974 | Babler | 558/430 |
| 3,895,078 | 7/1975 | Gueldner et al. | 568/839 |
| 4,152,355 | 5/1979 | Traas | 568/434 |
| 4,929,441 | 5/1990 | Flint et al. | 424/84 |

OTHER PUBLICATIONS

Bedoukian, Robert H. et al. "A Biogenetic-Type Synthesis of the Cyclohexyl Constituents of the Boll Weevil Pheromone" J. Org. Chem., vol. 40(15), 1975, pp. 2154–2156.

J. H. Tumlinson et al., "Sex Pheromones Produced by Male Boll Weevil: Isolation, Identification, and Synthesis," Science 166: 1010–1012 (Nov. 1969).

D. D. Hardee et al., "Response of Boll Weevils to Component Ratios and Doses of the Pheromone, Grandlure," Environmental Entomology 3(1):135–138 (Feb. 1974).

R. J. Patrock et al., "Field Evidence for an Attractant Produced by the Male Pepper Weevil (Coleoptera: Curculionidae)," Florida Entomologist 75(1):138–144 (Mar. 1992).

D. L. Goudriet et al., "Bioassay Procedure for an Attractant of the Pepper Weevil (Coleoptera: Curculionidae)," Journal of Economic Entomology, 81(5):1499–1502 (Oct. 1988).

*Primary Examiner*—Allen J. Robinson
*Assistant Examiner*—John D. Pak
*Attorney, Agent, or Firm*—M. Howard Silverstein; Curtis P. Ribando; John D. Fado

[57] ABSTRACT

Synthetically prepared pheromone compositions, prepared from various mixtures of (Z)-3,3-dimethyl-$\Delta^{1,\beta}$-cyclohexane ethanol, (E)-3,3-dimethyl $\Delta^{1,\beta}$-cyclohexane ethanol, (Z)-3,3-dimethyl-$\Delta^{1,\alpha}$-cyclohexane acetaldehyde, (E)-3,3-dimethyl-$\Delta^{1,\alpha}$-cyclohexane acetaldehyde, (E)-3,7-dimethyl-2,6-octadienoic acid, and (E)-3,7-dimethyl-2,6-octadien-1-ol were found to be attractive to both male and female pepper weevils. The compositions will greatly enhance pepper growers' ability to control these destructive pests.

17 Claims, No Drawings

COMPOSITIONS FOR THE CONTROL OF PEPPER WEEVILS

BACKGROUND OF THE INVENTION

FIELD OF THE INVENTION

This invention relates to synthetically prepared aggregation pheromones of the pepper weevil, *Anthonomus eugenii* Cano (Coleoptera: Curculionidae), and the use of these pheromones to aid in insect control, for example, in pheromone-baited traps.

REFERENCES

Throughout this application, various publications are referenced by the name of the author and date of publication within parentheses. Full citations for these references may be found at the end of the specification, listed in alphabetical order.

DESCRIPTION OF THE PRIOR ART

The pepper weevil, *Anthonomus eugenii* Cano (Coleoptera: Curculionidae), is an important pest of both sweet and hot peppers (Capsicum spp.) in the southern United States and throughout Central America (Elmore et al., 1934; Goff and Wilson, 1937). The most important damage is yield reduction resulting from premature abscission of infested fruit. Infested fruit not aborted may contain frass and decaying plant tissue making them unmarketable. Additionally, the pepper weevil has been implicated in the transmission of an internal mold of peppers (Bruton et al., 1989).

Weevil eggs are deposited into pepper pods or buds where larval development takes place. Since insecticides cannot reach the protected larvae, treatments must be directed against the adults and should be started before significant infestation occurs. Current control practices are to apply chemicals every 5 to 7 days until the crop matures (Coudriet and Kishaba, 1988). However, effective chemical control of adult peppers weevils is hindered by problems associated with detecting adults prior to economic injury (Genug and Osaki, 1972). Visual sampling is used to time pesticide applications, but this method is inefficient. Sticky traps have been used, but the correlation of population density to trap catch is weak (Patrock et al., 1992). Predictive models for pepper weevil adult emergence are unavailable and decisions regarding adulticide treatments and timing are generally based on classical "calendar" spraying regimes (Riley, 1990). Action thresholds for the pepper weevil are low: 5% terminal bud damage (Cartwright et al., 1990) and between 1 adult/400 terminals (Riley, 1990) and 1 adult/100 terminals (Andrews et al., 1986). Because the above-mentioned sampling methods are tedious, time-consuming and may only detect weevils after damage has passed economic levels, a better monitoring system is needed for this pest.

Live male pepper weevils have been shown to attract females and males in the field (Patrock et al., 1992). However, the nature of the male-produced attractant was not determined. A synthetic pheromone, if available, could provide a reliable and economic method for determining pepper weevil presence and determining density for making management decisions.

SUMMARY OF THE INVENTION

We have elucidated the components of a multi-component, male-produced aggregation pheromone emitted by *Anthonomus eugenii* Cano, and surprisingly found that various synthetic mixtures of the component compounds are effective in attracting both males and females of the species.

It is an object of this invention to describe these compounds and mixtures and their use in attracting and/or destroying the insects.

Other objects and advantages of the invention will become readily apparent from the ensuing description.

DETAILED DESCRIPTION OF THE INVENTION

We have discovered that male *Anthonomus eugenii* Cano produce an aggregation pheromone which is a complex mixture of volatile terpenoids. Several compounds of this mixture were identified and were shown to be attractive to both sexes in various combinations. These compounds are herein designated:

PWI (Z)-3,3-dimethyl-$\Delta^{1,\beta}$-cyclohexane ethanol
PWII (E)-3,3-dimethyl-$\Delta^{1,\beta}$-cyclohexane ethanol
PWIII (Z)-3,3-dimethyl-$\Delta^{1,\alpha}$-cyclohexane acetaldehyde
PWIV (E)-3,3-dimethyl-$\Delta^{1,\alpha}$-cyclohexane acetaldehyde
PWV (E)-3,7-dimethyl-2,6-octadienoic acid (geranic acid)
PWVI (E)-3,7-dimethyl-2,6-octadien-1-ol (geraniol)

The structures of PWI–VI are as follows:

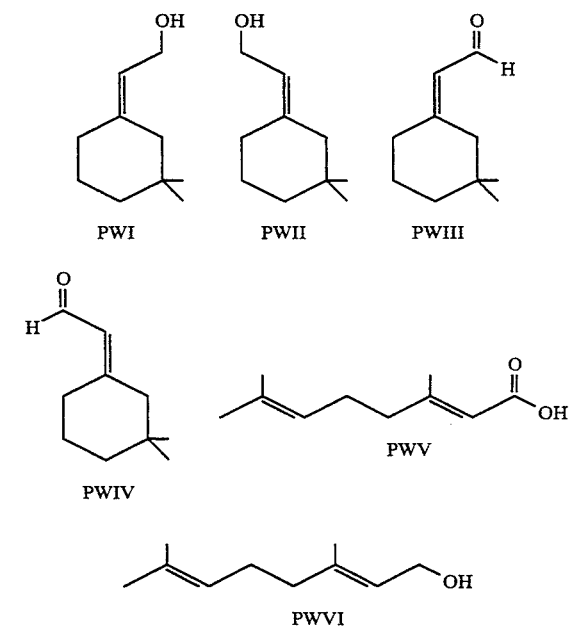

Analysis of Pheromone Volatiles

Insects: A laboratory culture of pepper weevils was established from insects collected in Florida and Texas. Pepper weevils were reared according to known methods (Patrock, 1986). Fresh jalepeno peppers were purchased locally, grown in a greenhouse or grown in an outdoor garden. Emerging adult pepper weevils were held individually in 30 ml diet cups and fed sliced fresh jalepeno pepper, black nightshade berries, or a piece of artificial diet (Toba et al., 1969) Adult pepper weevils were sexed using $CO_2$ anesthetization and characters as described for sexing boll weevils (Agee, 1964). In addition, males can be identified by the presence of a large, hooked metatibial spur (i.e., mucro).

Collection of Volatiles: Initially, volatiles were collected using a 50 ml filtering flask and a "Tenax" porous polymer trap system (Bartelt et al., 1990). Later volatile collections were made using volatile collection system consisting of a 20 cm×2.2 cm ID "Pyrex" glass tube sealed on each end with a #11 cork stopper. One cork held a prefilter comprising a glass tube (7 cm×4 mm ID) containing a 6-mm plug of porous polymer beads ("Super Q," 80/100 mesh; Alltech Associates, Inc., Deerfield, Ill. This plug was packed between a stainless steel screen (325 mesh) at the bottom of the tube and a glass wool plug at the top. The other cork held a similar prefilter with "Super Q" about 4 mm thick to collect volatiles. Air was drawn through the tube with either the house vacuum system or vacuum pump at a flow of about 130 ml/min.

Volatiles were collected from both male and female pepper weevils to identify male-specific compounds (i.e., the putative aggregation pheromone components). Typically, volatiles were collected from individual pepper weevils on small (i.e., about 5 cm or shorter) jalepeno fruit, although occasionally volatiles were collected from groups of weevils and the plant material was pepper buds or nightshade berries. Collections were made for periods of 1-5 days, and collected volatiles were extracted using 240 µl hexane for "Tenax" Filters and methylene chloride or hexane for "Super Q" filters. Ten µl of a 250 ng/µl solution (i.e., 2500 ng) of α-terpineol was added to each filter extract as an internal standard to quantify collected volatiles.

Chromatographic Analyses: Gas chromatography was performed using two different systems. The first (HP-5) was a "Hewlett-Packard 5890 Series II" gas chromatograph (GC), a "Spectra-Physics SF4400" integrator, and a fused silica "Hewlett-Packard HP-5" column (0.17 µm film thickness, 25 m×0.32 mm ID, Hewlett Packard Co., Avondale, Pa.). The second ("DB-1") was a "Varian Model 3700" GC, a "Hewlett-Packard 3396A" integrator, and a fused silica "Durabond DB-1" column (1.0 µm film thickness, 15 m×0.25 mm ID) (J & W Scientific, Folsom, Calif.). The temperature programs were: 50° C. for 3 min, then 10° C./min to 220° C. and 70° C. to 200° C. at 10° C./min, respectively. For both gas chromatographs, the injector and detector temperatures were 170° C. and 250° C., respectively, and each was equipped with a flame ionization detector with helium as the carrier gas. One to two µl were injected and injections were made in the splitless mode and after 0.60 min changed to the split mode.

A comparison of the GC profiles of volatile collections of males and females revealed the presence of at least six compounds specific to males. These compounds were designated PWI through PWVI.

Retention indices (RI) were calculated using n-alkane standards (Poole and Schuette, 1984). The RI for compounds PWI, PWII, PWIII, PWIV, PWV, and PWVI on the "DB-1" column were: 12.14, 12.16, 12.33, 12.40, 13.33, and 12.40 respectively. The RI for compounds PWI-VI on the "HP-5" column were 12.24, 12.27, 12.50, 12.59, 13.62, and 12.52, respectively.

Release rates of compounds PWI-PWVI were determined by collecting volatiles, as described above, for a set length of time, usually 24 hours, and adding a known amount of an internal standard to the extract of the collection filter. When the volatiles were analyzed by gas chromatography, the area under the peak representing the internal standard was compared to the area under the peaks representing PWI-PWVI. In this manner, relative amounts of each component of the pheromone volatiles were determined. Dividing the amount of each component by the length of the collection for a number of collections gave average release rates of about 7.20, 4.80, 0.45, 0.30, 1.95, and 0.30 µg/male-day for PWI, PWII, PWIII, PWIV, PWV, and PWVI, respectively.

Gas Chromatography—Mass Spectrometry: Electron-impact mass spectra (EI-MS) were obtained on a "Hewlett-Packard 5970 Mass Selective Detector." An ionizing potential of 70 eV was used for EI spectra. Sample introduction was through a "Hewlett-Packard 5890" GC fitted with a "DB-1" (0.25 µm film thickness, 15 m×0.25 mm ID) capillary column. Chemical-ionization mass spectra (CI-MS) were performed on a "Finnigan 4535" quadrapole mass spectrometer. The reagent gas was isobutane. Sample introduction was through a GC fitted with a "DB-1" (0.25 µm film thickness, 15 m×0.25 mm ID) capillary column.

Proton Nuclear Magnetic Resonance Spectroscopy ($[^1H]NMR$): Nuclear magnetic resonance (NMR) proton spectra were obtained on a Bruker 300 Mhz instrument using deuterochloroform as the solvent. Shifts are reported in parts per million ($\delta$) relative to tetramethylsilane.

Infrared Spectroscopy: Vapor phase fourier transform infrared (FTIR) spectra were obtained using a "Mattson Galaxy Series 6020 FT-IR". Samples were introduced through the "Hewlett Packard 5890" GC and column described earlier using the same temperature program. Absorptions are reported in reciprocal centimeters.

High Performance Liquid Chromatography: Prior to proton nuclear magnetic resonance spectroscopy, all compounds were purified by high performance liquid chromatography (HPLC). HPLC separations were performed using a "Spectra Physics SP8700" solvent delivery system and "Spectra Physics SP8750" pump and "Waters R401" refractive index detector. A silica column (5 µm; 4.6 mm dia×250 mm long) was used, and the mobile phase was 25% ether in hexane at a flow rate of 1 ml/min.

Synthetic Chemicals: Synthetic compound PWI was purchased from Frank Enterprises, Inc. (Columbus, Ohio, 95% pure by GC). Synthetic compound PWII (98% pure by GC) and a mixture of PWIII and PWIV (95% pure by GC) were purchased from Bedoukian Research, Inc. (Danbury, Conn.). Synthetic compound PWV was purchased from ICN Biomedicals, Inc. (Cleveland, Ohio, 59% pure by GC). Synthetic compound PWI was purchased from Aldrich Chemical Co. (Milwaukee, Wis., 98% pure by GC). These synthetic chemicals were used as purchased without purification for field assays with 0.5% BHT added as a preservative.

Analyses: EI-MS analyses of compounds PWI and PWII revealed they had very similar spectra with molecular ions at m/z 154, which corresponds to a molecular formula of $C_{10}H_{18}O$ (2 degrees of unsaturation). A search of the National Bureau of Standards Mass Spectral Library showed that both PWI and PWII gave an essentially perfect match with (Z)-3,3-dimethyl-$\Delta^{1,\beta}$-cyclohexane ethanol. Since PWI and PWII had different retention times on GC, PWI was tentatively identified as (Z)-3,3-dimethyl-$\Delta^{1,\beta}$-cyclohexane ethanol and PWII as (E)-3,3-dimethyl-$\Delta^{1,\beta}$-cyclohexane ethanol.

Synthetic standards of these two compounds matched GC retention times of pepper weevil-derived compounds on both GC columns. Both mass spectral analyses and NMR analyses gave identical spectra for the pepper weevil-derived and the synthetic compounds. Compound PWI showed EI ions at m/z (% base) 154 (5), 136 (31), 121 (31), 95 (20), 93 (41), 81 (24), 79 (25), 69 (76), 67 (27), 57 (29), 55 (37), 43 (42), 41 (100). Compound PWI had [$^1$H]NMR $\delta$(ppm) 0.88 (6H, s), 1.35 (2H, m), 1.55 (2H, m), 1.95 (2H, s), 2.04 (2H, t), 4.10 (2H, m), 5.47 (1H, m). Compound PWII showed EI ions at m/z (% base) 154 (5), 136 (32), 121 (24), 95 (29), 93 (54), 81 (27), 79 (31), 69 (73), 67 (31), 57 (14), 55 (36), 43 (27), 41 (100). Compound PWII had [$^1$H]NMR $\delta$(ppm) 0.86 (6H, s), 1.34 (2H, m), 1.51 (2H, m), 1.87 (2H s), 2.11 (2H, t), 4.15 (2H, d), 5.31 (1H, m).

PWIII and PWIV produced mass spectra with molecular ions at m/z 152, two units less than alcohols PWI and PWII. By analogy to the boll weevil system, these compounds were compared with standards of the aldehydic boll weevil compounds (Tumlinson et al., 1969). These matched exactly by GC and mass spectrometry. Thus, PWIII and PWIV correspond to (Z)- and (E)-3,3-dimethyl-$\Delta^{1,\alpha}$-cyclohexane acetaldehyde, respectively. Compound PWIII showed EI ions at m/z (% base) 152 (28), 137 (67), 119 (7), 109 (42), 95 (14), 81 (41), 69 (58), 67 (26), 57 (16), 55 (23), 43 (30), 41 (100). Compound PWIV showed EI ions at m/z (% base) 152 (40), 137 (28), 119 (12), 109 (63), 95 (35), 81 (40), 69 (58), 67 (33), 57 (26), 55 (23), 43 (49), 41 (100).

EI-MS analysis of compound PWV did not reveal an obvious molecular ion. CI-MS analysis of compound PWV gave a base peak (M+1) at m/z 169, which corresponds to a molecular formula of $C_{10}H_{16}O_2$ (3 degrees of unsaturation). FTIR analysis and library search (EPA) of this compound suggested that it was an unsaturated carboxylic acid. Subsequent EI-MS analysis of the methyl ester derivative gave a molecular ion at m/z 182, which corresponds to molecular formula of $C_{11}H_{18}O_2$ (3 degrees of unsaturation). A search of the mass spectra library gave an essentially perfect match with methyl (E)-3,7-dimethyl-2,6-octadienoate (geranic acid methyl ester). Therefore, compound PWV was tentatively identified as (E)-3,7-dimethyl-2,6-octadienoic acid (geranic acid). A synthetic standard of geranic acid matched the GC retention times of the weevil-derived compound on both GC columns. Mass spectral analyses and NMR analyses gave identical spectra for the pepper weevil-derived and the synthetic compound. Compound PWV showed EI ions at m/z (% base) 168 (1), 151 (2), 125 (6), 123 (18), 111 (1), 100 (18), 99 (3), 85 (5), 82 (8), 69 (100), 67 (9), 53 (6), 41 (55). FTIR of compound PWV gave absorptions (cm$^{-1}$) (gas) 3585 (m), 2971 (m), 2933 (m), 2871 (m), 1752 (s), 1652 (m), 1107 (s). Compound PWV had [$^1$H]NMR $\delta$(ppm) 1.60 (3H, br s), 1.68 (3H, br s), 2.16 (4H, d), 2.17 (3H, br s), 5.06 (1H, m), 5.69 (1H br s). The methyl ester of compound PWV showed EI ions at m/z (% base) 182 (2), 167 (1), 151 (9), 139 (8), 123 (35), 122 (11), 114 (35), 83 (22), 82 (12), 69 (100), 67 (8), 53 (7), 41 (47).

Mass spectral analaysis of compound PWVI suggested it was a terpene alcohol, and PWVI was found to match synthetic geraniol by GC and mass spectrometry. Compound PWVI showed EI ions at m/z (% base) 154 (10), 139 (1), 136 (2), 123 (5), 121 (3), 111 (3) 93 (8), 84 (6), 83 (4), 69 (68), 68 (15), 67 (13), 55 (10), 53 (16), 43 (12), 41 (100).

The synthetically prepared pheromone compositions of the invention are made up of suitable mixtures of the compounds PWI and PWII, and optionally PWIII, PWIV, PWV, and PWVI. These compositions are useful in capturing and/or killing pepper weevils when applied to traps and the like in pepper weevil attractive amounts. Suitable component ratios were determined by collecting over one hundred separate volatile samples, as described above, analyzing each sample by gas chromatography, and integrating peak areas against an internal standard (Table I). When one or more of PWIII, PWIV, PWV, or PWVI is incorporated into the composition, it should be present in an amount of at least 1%, and preferably at least 5%, relative to the other compounds in order to have a noticeable effect.

TABLE I

| Compound | % of Compound in Composition pheromone mixture |
|---|---|
| PWI | 33–71 |
| PWII | 29–67 |
| PWIII | 0–6 |
| PWIV | 0–6 |
| PWV | 0–70 |
| PWVI | 0–6 |

Volatiles collected from five or more males together sometimes contained as much as 70% compound PWV. Preferably the ratio of PWI:PWII is about 60:40 and the ratio of PWI:PWII:PWIII:PWIV:PWV:PWVI is about 48:32:3:2:13:2. A suitable total release rate of pheromone components is at least about 0.5 $\mu$g/hr, preferably about 40 $\mu$g/hr. The compound PWVI is present in the collected volatiles in very small amounts, and was not included in the synthetically prepared mixtures for the initial field studies (Examples 1 and 2). However, it is believed that the inclusion of PWVI in the synthetically prepared mixtures may enhance the mixtures attractiveness. All ratios and percentages cited herein are by weight unless otherwise stated.

The synthetic prepared pheromone compositions can be used alone or may be combined in effective amounts with inert carriers or other attractants such as host plant volatiles, especially from damaged plants, and other pheromones. In this manner, the insects are attracted for the purpose of monitoring to determine pepper weevil presence and density. The pheromones may also be combined with effective amounts of insecticides to attract and destroy the insects.

The term "effective amount" as applied to the pheromone compositions and other active agents contemplated for use in the invention is defined herein to mean any amount which will produce a statistically significant effect in comparison to the observed result of a control composition which does not contain the agent. An effective amount of pheromone composition is any amount which is attractive to pepper weevils.

The synthetically prepared pheromone compositions may be applied to the habitat of pepper weevils by using any of the pheromone dispensers and application methods known to those skilled in the art. Particularly suitable are traps such as the bait stick (Konstant, 1990) or commercially available sticky traps (Great Lakes IPM, Vestaburg, Mich.).

It will be appreciated by those skilled in the art of insect pheromones that the ratios of components of the pheromone mixtures of the invention may be varied depending on field conditions such as temperature, humidity, wind velocity and insect population.

The following examples are intended only to further illustrate that which the inventors believe to be their invention and are not intended to limit the scope of the invention which is defined by the claims.

EXAMPLE 1

Field Assays: Field-trials of synthetically prepared compositions were conducted in the Spring of the year in pepper fields at several locations in Florida using commercial boll weevil traps (Great Lakes IPM, Vestaburg, Mich.). Traps were placed on bamboo stakes just above plant height and were separated by about 10-m. Both unbaited control traps and baited traps contained a small piece (1-cm$^3$) of "Pest Strip" (Loveland Industries, Inc., Greely, Colo.) to kill captured insects. Traps were checked at 3- to 5-day intervals and were rotated at each check.

Various dosages of the 5-component blend and were compared to individual components and combinations of components. Five release rates (relative dosage) were tested: 0.5 µg/hr (0.1×), 1.5 µg/hr (0.3×), 4.5 µg/hr (1×), 14 µg/hr (3×), and 40 µg/hr (9×). These treatments released the 5-component blend (i.e., compounds PWI, PWII, PWIII, PWIV, and PWV) in a ratio of about 48:32:3:2:15. When individual components or other subsets of components were formulated, the absolute amount of each component was the same as the amount of that component in the 5-component, 1× blend. Compounds PWI, PWII, PWIII, and PWIV were formulated in "Teflon" capillaries (0.107 mm or 3.175 mm ID) and compound PWV was formulated on poly discs (supplied by TRECE, Inc., Salinas, Calif.). Four replications were set up in commercial pepper fields in Florida. Tests 1 and 2 were conducted in a commercial pepper field near Felda, Fla., from March 1 to April 15. Tests 3 and 4 were conducted in pepper fields near West Palm Beach from March 3–30, and in Immokalee, Fla., from April 8–27, respectively. There were two replications of control traps and one replication of all other treatments at each location. Pheromone baits were replaced once during these tests.

Trap capture data (total captures over period) were analyzed using Friedman's Rank Sums (Conover, 1980). Additionally, the dose-response data were analyzed for linear and higher order polynomial effects for pheromone dosage on trap captures after analysis of variance. Significance levels were 0.05 for all tests.

The results of the field trials of the dosage and component tests are shown in Table 2. Traps baited with the highest dosage of pheromone (i.e., 9.0×) captured the most pepper weevils and captured significantly more pepper weevils than control traps. In addition, the 5-component blend PWI−PWV (0.3×) and PWI+PWII treatments captured significantly more pepper weevils than did control traps. The number of pepper weevils captured increased significantly with pheromone dosage (linear contrast, $F_{1,234}=11.6$, $P<0.001$). The higher order polynomial terms were not significant, however (overall, $F_{3,234}=2.0$, $P>0.05$). PWI−PWV (1×) captured significantly more pepper weevils than PWI, PWII, PWIII+PWIV and the 4-component blend PWI−PWIV. In addition, PWI+PWII captured significantly more pepper weevils than PWI, PWII, PWI+PWII+PWV and PWI−PWIV. Control traps captured 33% females (totaled over location) while traps containing the 5-component blend captured 53% females (totaled over dosage and location). Traps containing PWI+PWII captured 61% females (totaled over location). The results are reported in Table II below.

TABLE II

| Treatment[1] | Total Trap Captures Over Test Period | | | |
|---|---|---|---|---|
| | Test 1 | Test 2 | Test 3 | Test 4 |
| Control[2] ab | 4.5 | 3.5 | 0 | 0 |
| PWI − PWV (0.1X) abc | 2 | 4 | 6 | 0 |
| PWI − PWV (0.3X) de | 14 | 7 | 6 | 2 |
| PWI − PWV (1X) bcde | 6 | 7 | 3 | 1 |
| PWI − PWV (3X) abcd | 13 | 2 | 2 | 4 |
| PWI − PWV (9X) e | 12 | 16 | 11 | 6 |
| PWI a | 2 | 1 | 4 | 0 |
| PWII a | 3 | 2 | 3 | 0 |
| PWI + PWII cde | 5 | 19 | 8 | 1 |
| PWIII + PWIV a | 3 | 2 | 1 | 0 |
| PWV abc | 4 | 3 | 5 | 0 |
| PWI + PWII + PWV ab | 0 | 2 | 4 | 1 |
| PWI − PWIV a | 1 | 3 | 3 | 0 |

[1]Treatments without letters in common differ significantly (Friedman Rank Sums).
[2]There were two replications of control traps per location and the mean number captured is given.

EXAMPLE 2

In the same manner as Example 1, a 5-component blend (i.e., PWI−PWV) at a release rate of 14 µg/hr (3×) was compared to control traps. Pheromone components or mixtures thereof were formulated with BHT as an antioxidant and a solid carrier. The general procedure consisted of adding BHT to the pheromone blend to be tested to get a mixture containing 1% (by weight) BHT. This mixture was subsequently mixed with the carrier so that the pheromone was present at a level of about 8% (by weight). PWVI (geranic acid) was formulated separately and was mixed with an equal amount of mineral oil (Fischer Scientific, Fairborn, N.J.) to slow the release of this compound, otherwise the general procedure was used. Approximately 0.5 g of each mixture was placed inside a controlled release dispenser.

Four tests were set up in pepper fields in Florida during the summer. Test 1 was in Felda from June 4–23, Test 2 was in Immokalee from June 9–16, Test 3 was in Delray Beach from May 7 to June 7, and Test 4 was in Bradenton from June 5–30. The fields near Felda and Delray Beach were commercial pepper fields. The fields near Immokalee and Bradenton were in University of Florida Experiment Station pepper fields. There were five replications of each treatment tested at each location, and pheromone baits were replaced once during the tests. The results of the field trials are shown in Table III. Traps containing the 5-component blend (3×) captured significantly more pepper weevils than did control traps. The total number captured in pheromone baited traps was over six times that caught in control traps. The PWI−PWV blend captured 64% females (totaled over location).

TABLE III

| Treatment | Total Trap Captures Over Test Period | | | |
|---|---|---|---|---|
| | Test 1 | Test 2 | Test 3 | Test 4 |
| Control | 7 | 6 | 1 | 0 |
| PWI − PWV (3X)[1] | 14 | 29 | 32 | 12 |

[1]PWI − PWV (3X) caught significantly more pepper weevils than control traps (Friedman Rank Sums Test).

EXAMPLE 3

In an effort to increase the efficiency of trapping pepper weevils, a third experiment was designed to compare boll weevil traps with sticky traps. The 6-component blend (i.e., PWI—VI) at a release rate of 14 μg/hr (3×) was compared to unbaited control traps. This field test was conducted during November to December in a pepper field near Weslaco, Tex., and in a 2-acre greenhouse with peppers near Oxnard, Calif. Four treatments were compared: unbaited (control) boll weevil traps, boll weevil traps baited with the 6-component blend, unbaited (control) sticky traps (6"×12" yellow strips, Olson Products, Medina, Ohio), and sticky traps baited with the 6-component blend. The pheromone blend was formulated (using the new formulation described in Example 2) to release the 6-component blend in a 48:32:3:2:13:2 weight ratio for compounds I, II, III, IV, V, and VI, respectively. Pheromone baits were placed inside the boll weevil traps as described earlier and were attached near the top of the sticky traps using a thumb tack. There were five replications of each treatment, and the traps were checked at 2- to 5-day intervals a total of six times.

The results of the field trials comparing boll weevil traps and sticky traps are shown in Table IV. In Texas, neither the unbaited nor the baited boll weevil traps captured any pepper weevils. The unbaited sticky traps captured a total of two weevils during this test while the pheromone-baited sticky traps captured a total of 41 pepper weevils. In California, the unbaited and baited boll weevil traps captured two and four pepper weevils, respectively. The baited sticky traps captured a total of 72 pepper weevils. The pheromone-baited sticky traps captured significantly more pepper weevils than did any of the other treatments at both locations.

TABLE IV

Texas and California Field Data for Synthetic Pheromone (New Formulation): Total Trap Captures Over Test Period

| Treatment[1] | Location (test period) | |
|---|---|---|
|  | Weslaco, TX (11/18–12/2) | Oxnard, CA (11/21–12/7) |
| Unbaited boll weevil trap | 0 a | 2 a |
| Baited boll weevil trap | 0 a | 4 a |
| Unbaited sticky trap | 2 a | —[2] |
| Baited sticky trap | 41 b | 72 b |

[1]There were five replications of each treatment, numbers without letters in common differ significantly (Friedman Rand Sums).
[2]There were no unbaited sticky traps in this study.

REFERENCES

Agee, H. R. 1964. Characters for determination of sex of the boll weevil. J. Econ. Entomol. 57:500–501.

Andrews, K. L., Rueda, A., Gandini, G., Evans, S., Arango, A., and Avedillo, M. 1986. A supervised control programme for the pepper weevil, Anthonomus eugenii Cano, in Hondurus, Central America Trop. Pest Manag. 32:1–4.

Bartelt, R. J., Dowd, P. F., Plattner, R. D., and Weisleder, D. 1990. Aggregation pheromone of dried fruit beetle, Carpophilus hemipterus: Wind tunnel bioassay and identification of two novel tetrene hydrocarbons. J. Chem. Ecol. 16:1015–1039.

Bruton, B. D., Chandler, L. D., and Miller, M. E. 1989. Relationship between pepper weevil and internal mold of sweet pepper. Plant Disease 73:170–173.

Cartwright, B., Teague, T. G., Chandler, L. D., Edelson, J. V., and Bentsen, G. 1990. An action threshold for management of the pepper weevil (Coleoptera: Curculionidae) on bell peppers. J. Econ. Entomol. 83:2003–2007.

Conover, W. J. 1980. Statistical Methods Based on Ranks: Practical Nonparametric Statistics, 2nd Ed. John Wiley & Sons, New York.

Coudriet, D. L. and Kishaba, A. N. 1988. Bioassay Procedure for an Attractant of the Pepper Weevil (Coleoptera: Curculionidae). J. Econ. Entomol. Vol. 8 No. 5:1499–1502.

Elmore, J. C., Davis, A. C., and Campbell, R. E. 1934. The pepper weevil. USDA Tech. Bull. 447.

Genug, W. G. and Osaki, H. Y. 1972. Pepper weevil on the Florida East Coast. Univ. Fla. AREC Belle Glade Mimeo Rpt. EV-1972-2.

Gibbons, J. D. 1985. Nonparametric Methods for Quantitative Analysis. American Sciences Press, Inc.

Goff, C. C. and Wilson, J. W. 1937. The pepper weevil. Univ. of Florid Agric. Exp. Stn. Bull. 310.

McKibben, G. H., Smith, J. W., and Villavaso, E. J. 1991. Field research results on the boll weevil bait stick. Proc. Beltwide Cotton Conf. 2:622–623.

Patrock, R. J. 1986. Observations on the behavior and host relations of the pepper weevil Anthonomus eugenii Cano (Coleoptera: Curculionidae) in Florida. MSc thesis, Univ. Fla., Gainesville, Fla.

Patrock, R. J., Schuster, D. J., and Mitchell, E. R. 1992. Field evidence for an attractant produced by the male pepper weevil (Coleoptera: Curculionidae). Flor. Entomol. 75:138–144.

Poole, C. F. and Shuette, S. A. 1984. Contemporary Practice of Chromatography. Elsevier, Amsterdam.

Riley, D. G. 1990. Refined sampling methodology and action thresholds for the pepper weevil, Anthonomus eugenii Cano (Coleoptera: Curculionidae). PhD dissertation., Univ. Fla., Gainesville, Fla.

Toba, H. H., Kishaba, A. N., Pangaldan, R. and Riggs, S. 1969. Laboratory rearing of pepper weevils on artificial diets. J. Econ. Entomo. 62:257–258.

Tumlinson, J. H., Hardee, D. D., Gueldner, R. X., Thompson, A. C., Hedin, P. A., and Minyard, J. P. 1969. Science. 166: 1010–1012.

We claim:

1. A composition for attracting pepper weevils comprising mixtures of:

(Z)-3,3-dimethyl-$\Delta^{1,\beta}$-cyclohexane ethanol (PWI);

(E)-3,3-dimethyl-$\Delta^{1,\beta}$-cyclohexane ethanol (PWII);

(Z)-3,3-dimethyl-$\Delta^{1,\alpha}$-cyclohexane-acetaldehyde (PWIII); and (E)-3,3-dimethyl-$\Delta^{1,\beta}$-cyclohexane-acetaldehyde (PWIV);

and further comprising at least one of the following compounds:

(E)-3,7-dimethyl-2,6-octadienoic acid (PWV); and (E)-3,7-dimethyl-2,6-octadien-1-ol (PWVI);

in amounts and in proportions that are effective to attract pepper weevils.

2. The composition of claim 1 wherein the weight ratio of PWI to PWII is about 60:40.

3. The composition of claim 1 wherein the relative amounts by weight are:

PWI 33–71%
PWII 29–67%
PWIII 1–6%
PWIV 1–6%
PWV 0–70%
PWVI 0–6% wherein at least one of PWV, or PWVI is present in an amount of at least 1% by weight.

4. The composition of claim 1 which further comprises an insecticide effective against pepper weevils in pepper weevil killing amounts.

5. The composition of claim 1 which further comprises pepper plant volatiles in pepper weevil attractive amounts.

6. The composition of claim 1 which further comprises a carrier.

7. A method of attracting pepper weevils comprising applying to the habitat of said pepper weevils an effective amount of the composition of claim 1.

8. A method of attracting pepper weevils comprising applying to the habitat of said pepper weevils an effective amount of the composition of claim 2.

9. A method of attracting pepper weevils comprising applying to the habitat of said pepper weevils an effective amount of the composition of claim 3.

10. The composition of claim 1 comprising PWI, PWII, PWIII, PWIV and PWV.

11. The composition of claim 1 comprising PWI, PWII, PWIII, PWIV, PWV, and PWVI.

12. A method of attracting pepper weevils comprising applying to the habitat of said pepper weevils an effective amount of the composition of claim 10.

13. A method of attracting pepper weevils comprising applying to the habitat of said pepper weevils an effective amount of the composition of claim 11.

14. A composition for attracting pepper weevils comprising mixtures of:
(Z)-3,3-dimethyl-$\Delta^{1,\beta}$-cyclohexane ethanol (PWI); and
(E)-3,3-dimethyl-$\Delta^{1,\beta}$-cyclohexane ethanol (PWII);
in amounts and in proportions that are effective to attract pepper weevils, and further comprising an insecticide effective against pepper weevils in pepper weevil killing amounts.

15. A composition for attracting pepper weevils comprising mixtures of:
(Z)-3,3-dimethyl-$\Delta^{1,\beta}$-cyclohexane ethanol (PWI); and
(E)-3,3-dimethyl-$\Delta^{1,\beta}$-cyclohexane ethanol (PWII);
in amounts and in proportions that are effective to attract pepper weevils, and further comprising pepper plant volatiles in pepper weevil attractive amounts.

16. A method of attracting pepper weevils comprising applying to the habitat of said pepper weevils an effective amount of the composition of claim 14.

17. A method of attracting pepper weevils comprising applying to the habitat of said pepper weevils an effective amount of the composition of claim 15.

* * * * *